(12) United States Patent
Lee et al.

(10) Patent No.: US 11,466,002 B2
(45) Date of Patent: Oct. 11, 2022

(54) METHOD FOR PREPARING A NON-RADIOACTIVE STANDARD β-CFT

(71) Applicant: INSTITUTE OF NUCLEAR ENERGY RESEARCH, ATOMIC ENERGY COUNCIL, EXECUTIVE YUAN, R.O.C., Taoyuan (TW)

(72) Inventors: Ching Yun Lee, Taoyuan (TW); Yu Chang, Taoyuan (TW)

(73) Assignee: INSTITUTE OF NUCLEAR ENERGY RESEARCH ATOMIC ENERGY COUNCIL, EXECUTIVE YUAN, R.O.C., Taoyuan (TW)

( * ) Notice: Subject to any disclaimer, the term of this patent is extended or adjusted under 35 U.S.C. 154(b) by 21 days.

(21) Appl. No.: 17/225,269

(22) Filed: Apr. 8, 2021

(65) Prior Publication Data

US 2022/0119380 A1   Apr. 21, 2022

(30) Foreign Application Priority Data

Oct. 21, 2020   (TW) ................................ 109136400

(51) Int. Cl.
*C07D 451/02*   (2006.01)
*C07B 49/00*   (2006.01)

(52) U.S. Cl.
CPC ............ *C07D 451/02* (2013.01); *C07B 49/00* (2013.01)

(58) Field of Classification Search
CPC ...................................................... C07D 451/02
USPC ........................................................... 546/132
See application file for complete search history.

(56) References Cited

PUBLICATIONS

Barr, Synthesis and Evaluation of Cocaine Analogs for Activity as Cocaine Anatagonists and Synthesis of Novel Prodrugs with Antiarthritic Potentail (1996), Theses and Dissertations, Med Univ of South Carolina.*

* cited by examiner

*Primary Examiner* — Taofiq A Solola
(74) *Attorney, Agent, or Firm* — Rosenberg, Klein & Lee

(57) ABSTRACT

This invention discloses method for preparing a non-radioactive standard β-CFT. Using cocaine hydrochloride as the starting material, and after a series of hydrolysis, dehydration, esterification and bonding reactions, a non-radioactive standard (2β-Carbomethoxy-3β-(4-fluoropenyl) tropane) is prepared. Furthermore, this preparation method has fewer steps, is easy to operate, and the purity of the product is as high as 97.97%. Therefore, the method for preparing a non-radioactive standard β-CFT can promote the development of positron imaging in the diagnosis of Parkinson's disease.

6 Claims, 3 Drawing Sheets

METHOD FOR PREPARING A NON-RADIOACTIVE STANDARD β-CFT

FIELD OF THE INVENTION

This invention relates to a method of making a standard product of contrast media, especially a method of making a non-radioactive standard β-CFT.

BACKGROUND OF THE INVENTION

According to the prediction of the World Health Organization, in 2040, neurodegenerative diseases will surpass cancers and become the second leading cause of human death. Therefore, many countries in the world including the United States, the EU, Japan, China, Canada, Australia and South Korea are vigorously developing the brain technology researches.

Population aging is a serious issue concerned by worldwide top researchers. There are approximately 6.3 million Parkinson's disease (PD) patients, 15 million Alzheimer's disease patients, 45 million schizophrenia patients and 300 million depression patients worldwide, causing a great burden on insurance resources and society.

However, Parkinson's disease is a long onset process, all of which are caused by neurodegeneration that leads to a decrease in dopamine secretion, which in turn leads to dyskinesias, such as sluggishness, stiffness, and tremor. At the current clinical diagnosis, SPECT imaging is still the main way used worldwide, yet its spatial resolution is lower than that of PET imaging technology. Therefore, nuclear medicines for the diagnosis of Parkinson's disease that can generate positron imaging will become a trend in future diagnosis.

In Taiwan, the main Parkinson's disease contrast media is [99mTc]TRODAT-1 developed by Professor Fan-yuan Kong of the University of Pennsylvania in Philadelphia, Pa. State, USA, and modified by the Institute of Nuclear Energy Research, AEC, and obtained the drug permit license of [99mTc]TRODAT-1 and became commercialization in 2005, which is a nuclear medicine for diagnosis of Parkinson's disease that produces single-photon images.

However, [99mTc]TRODAT-1 still has the following shortcomings: (1). The synthesis steps of TRODAT-1 active pharmaceutical ingredient are too cumbersome: the active pharmaceutical ingredient TRODAT-1 of [99mTc]TRODAT-1 requires a total of 11 steps for its synthesis, Too many synthetic process steps makes the total yield of [99mTc]TRODAT-1 unable to rise up.

Furthermore, (2). Concentration of heavy metals exceeding standard and making pollution: In the synthesis step of TRODAT-1 active pharmaceutical ingredients, the final step requires the removal of the protective group with a mercury-containing reagent to obtain the final product. In the case of using a mercury-containing reagent, the final product has the risk of containing excessive residual mercury and making pollution to the environment.

And, (3). Concerning about the supply of flag nuclides: the supply source of [99mTc] TRODAT-1 flag nuclides Tc-99m may become difficult due to the shutdown of the Canadian NRU reactor and the Dutch HFR reactor, resulting in an imbalance in the global Tc-99m supply chain or the price flying up of Tc-99m, causing major fluctuations in nuclear medicine.

Therefore, in order to improve the difficulty of preparation of conventional contrast media ([99mTc]TRODAT-1) and the high cost of preparation, technical personnel in this field are actively developing the nuclear medicines and related medications that can generate positron images for Parkinson's disease diagnosis.

SUMMARY OF THE INVENTION

The main purpose of this invention is to provide a method of making the non-radioactive standard β-CFT, which uses cocaine hydrochloride as the starting material and undergoes a series of hydrolysis, dehydration, esterification and bonding reactions to make the non-radioactive standard 2β-Carbomethoxy-3β-(4-fluoropenyl) tropane. This method has few steps and is easy to operate, and the purity of the product is as high as 97.97%. For this reason, the method of making this non-radioactive standard β-CFT can promote the development of PET in the diagnosis of Parkinson's disease.

In order to achieve the aforesaid purpose, this invention discloses a preparation method of non-radioactive standard β-CFT. The steps include: taking a cocaine hydrochloride and a hydrochloric acid for a hydrolysis reaction to form an ecgonine hydrochloride; take the ecgonine hydrochloride and a phosphorus oxychloride for a dehydration reaction to form a (R)-(-)-Anhydroecgonine methyl ester; and take the (R)-(-)-Anhydroecgonine methyl ester and a Grignard reagent for a bonding reaction to form a 2β-Carbomethoxy-3β-(4-fluoropenyl) tropane.

This invention provides an embodiment, the content of which is a preparation method of non-radioactive standard β-CFT, in which after the step of taking the ecgonine hydrochloride and a phosphorus oxychloride for a dehydration reaction, it further comprises the steps of: adding an anhydrous methanol for an esterification reaction.

This invention provides an embodiment, the content of which is a preparation method of non-radioactive standard β-CFT, in which the (R)-(-)-Anhydroecgonine methyl ester and a Grignard reagent in the step perform a bonding reaction, the Grignard reagent is the 4-fluorophenyl magnesium bromide.

This invention provides an embodiment, the content of which is a preparation method of non-radioactive standard β-CFT, in which before the step of a bonding reaction between the (R)-(-)-Anhydroecgonine methyl ester and a Grignard reagent, it further comprises the step of: dissolving the Grignard reagent in anhydrous dichloromethane and cooling it down to −50° C.

This invention provides an embodiment, the content of which is a preparation method of non-radioactive standard β-CFT, in the step that the (R)-(-)-Anhydroecgonine methyl ester and a Grignard reagent perform a bonding reaction, the bonding reaction is carried out under nitrogen environment.

This invention provides an embodiment, the content of which is a preparation method of non-radioactive standard β-CFT, in the step that the (R)-(-)-Anhydroecgonine methyl ester and a Grignard reagent form a bonding reaction, a trifluoroacetic acid is further added for the bonding reaction.

DETAILED DESCRIPTION

To enable the Review Committee members having deeper realization and understanding on the features and functions of this invention, we hereby put the embodiment and detailed explanation in below:

Due to the difficulty of preparing conventional contrast media ([$^{99}$mTc]TRODAT-1) and the high cost of preparation, it is necessary to actively develop nuclear medicines and related medicines for PET Parkinson's disease diagnosis. Therefore, this invention proposes a preparation method of non-radioactive standard β-CFT to solve the problems caused by the conventional technology.

Figure 1:
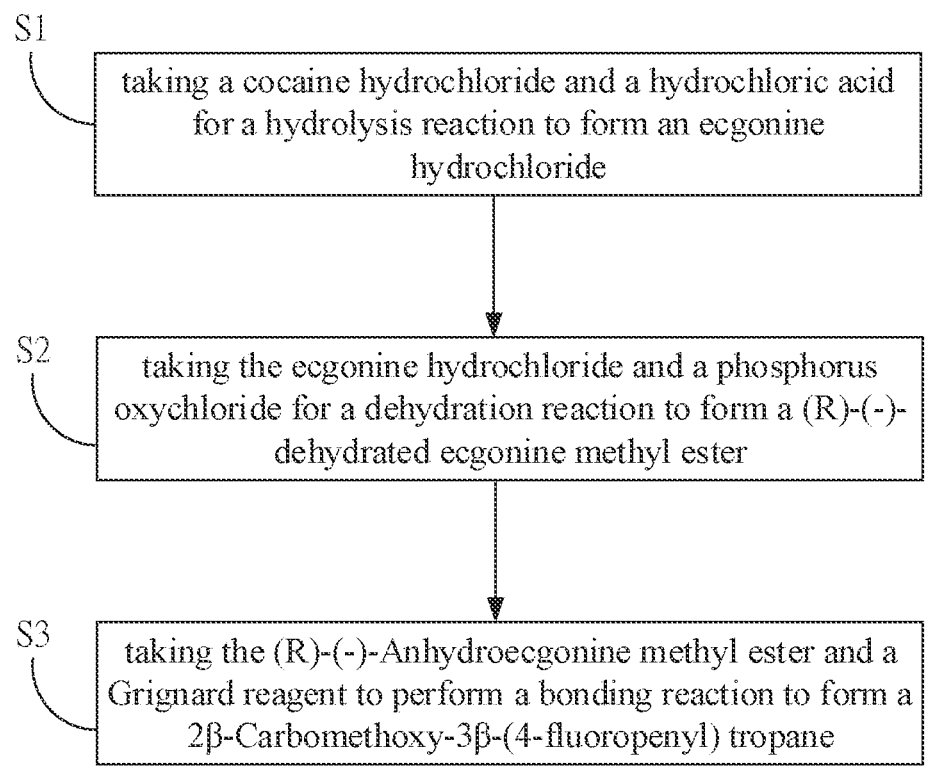
FIG. 1: The step flow diagram in an embodiment of this invention.
Figure 2:
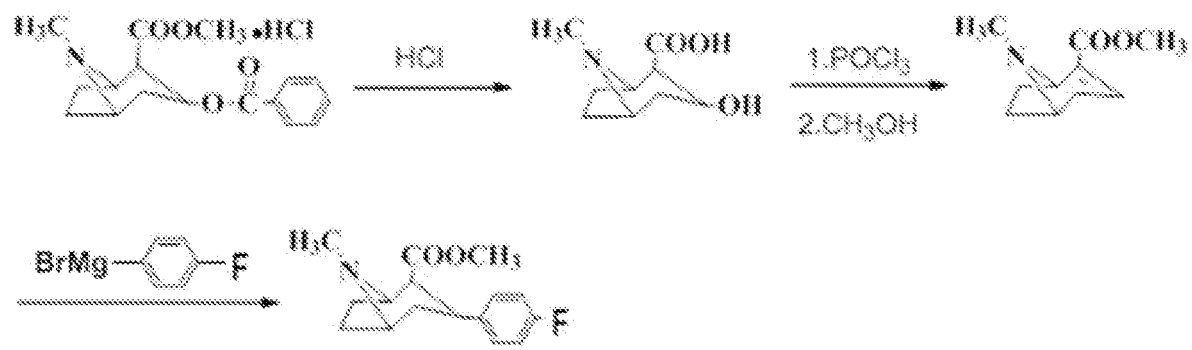
FIG. 2: The step route diagram in an embodiment of this invention.

The following will further explain the non-radioactive standard β-CFT preparation method of this invention, including the characteristics and the cooperated structure and the method:

First, refer to FIG. 1 and FIG. 2, which are the step flow diagram and step route diagram in an embodiment of this invention. As shown in the figures, this invention is the preparing method of a non-radioactive standard β-CFT; the steps include:

S1: Taking a cocaine hydrochloride and a hydrochloric acid for a hydrolysis reaction to form an ecgonine hydrochloride;

S2: Taking the ecgonine hydrochloride and a phosphorus oxychloride for a dehydration reaction to form a (R)-(-)-dehydrated ecgonine methyl ester; and S3: Taking the (R)-(-)-Anhydroecgonine methyl ester and a Grignard reagent to perform a bonding reaction to form a 2β-Carbomethoxy-3β-(4-fluoropenyl) tropane.

As shown in Step S1, take a cocaine hydrochloride (30.0 g, 99.6 mmol) and a hydrochloric acid (HCl, 0.8N, 200 mL) and put them into a 500 mL round-bottom flask to conduct a hydrolysis reaction under heating and refluxing, the reaction time is about 20 to 26 hours (preferably 24 hours); after the reaction solution is cooled to room temperature, it will precipitate the white solid. Making air-suction for filtration. After the liquid filtrate is taken, extract it with ether (3×300 mL). Discarding the organic phase and concentrate the aqueous phase by pressure reduction (at 80° C.) and then flushed with chloroform. With the method of air-suction and filtration, an ecgonine hydrochloride (18.4 g, the yield is 100%) is formed and obtained by the hydrolysis reaction.

The analytical data of the ecgonine hydrochloride of this invention is as follows: IR (neat): $v_{OH}$=3284 cm$^{-1}$, $v_{CO}$=1610 cm$^{-1}$.

$^1$H-NMR (CD$_3$OD): δ4.35 (m, 1 H, H3), 4.10 (d, 1 H, H$_1$), 3.88 (m, 1 H, H$_5$), 3.15 (dd, 1 H, H$_2$), 2.82 (s, 3 H, NCH$_3$), 2.36 (m, 2 H, H$_6$ and H$_7$), 2.10 (m, 3 H, H$_4$ and H$_6$ and H$_7$).

$^{13}$C NMR (CD$_3$OD): δ176.79 (CO), 65.82 (C3), 64.70 (C1), 61.46 (C$_5$), 49.00 (C$_2$), 39.23 (NCH$_3$), 36.86 (CH$_2$), 24.92 (CH$_2$), 24.19 (CH$_2$).

ESI-MS: m/z 186 (M$^+$-1), 141 (M$^+$-1 —COOH).

Meanwhile, as shown in Step S2, take the ecgonine hydrochloride (18.4 g, 99.5 mmol) and a phosphorus oxychloride (POCl$_3$, 100 mL) for a dehydration reaction under heating and refluxing for about 2 to 5 hours (preferably 3 hours), after the excess phosphorus oxychloride is distilled off under reduced pressure, Step S21 is further included in the ice bath state: Adding an anhydrous methanol (CH$_3$OH, 100 mL) to perform an esterification reaction (in after dissolving completely, stir at room temperature until the next day), and then distill off the excess of the anhydrous methanol under reduced pressure. Next, dissolve the residue with water (150 mL), basify it with sodium hydroxide, and then extract the product by dichloromethane (3×100 mL). Dry up the organic phase with sodium sulfate (Na$_2$SO$_4$), concentrated under reduced pressure, and reacted to form a (R)-(-)-Anhydroecgonine methyl ester (15.6 g, the yield is 87%).

The analysis data of the (R)-(-)-Anhydroecgonine methyl ester of this invention is as follows: IR (neat): $v_{CO}$=1730 cm$^{-1}$.

$^1$H-NMR (CDCl$_3$): δ6.81 (m, 1 H, H$_3$), 3.98 (d, J=5.6 Hz, 1 H, H$_1$), 3.94 (s, 3 H, OCH$_3$), 3.45 (m, 1 H, H$_5$), 2.83 (d, br, J=19.8 Hz, 1 H, H$_4$), 2.54 (s, 3 H, NCH$_3$), 2.36 (m, 2 H, H$_6$ and H$_7$), 2.04 (m, 2 H, H$_4$ and H$_7$), 1.72 (m, 1 H, H$_6$).

$^{13}$C NMR (CDCl$_3$): δ173.10 (CO), 166.12 (C$_2$), 135.81 (C$_3$), 58.10 (C$_1$), 56.32 (C$_5$), 51.06 (OCH$_3$), 36.00 (NCH$_3$), 34.01 (CH$_2$), 31.66 (CH$_2$), 29.88 (CH$_2$).

ESI-MS: m/z 181 (M$^+$), 166 (M$^+$ —CH$_3$), 152 (M$^+$ —CH$_3$—CH$_2$), 150 (M$^+$ —OCH3), 138 (M$^+$ —CH$_3$—(CH$_2$)$_2$), 122 (M$^+$ —COOCH$_3$).

Finally, as shown in Step S3, have the (R)-(-)-Anhydroecgonine methyl ester be pre-dissolved in an anhydrous dichloromethane (50 mL), and then making a bonding reaction with a Grignard reagent (5.8 mL, 0.030 mol, the Grignard reagent is a 4-F PhMgBr, 2M dissolved in ether) (under nitrogen environment), the Grignard reagent is dissolved in the anhydrous dichloromethane (250 mL) in advance and is cooled down to −50° C.

The bonding reaction of this invention is to slowly drop the (R)-(-)-Anhydroecgonine methyl ester into the Grignard reagent, and during the dripping reaction, keep it at about −50° C., stir for 2 to 5 hours (preferably 3 hours) and then cool down to −78° C. And in the step of the bonding reaction, further add a trifluoroacetic acid (2.42 mL, 0.030 mol, dissolved in 10 mL of anhydrous dichloromethane), stir the mixed solution for 30 minutes making reaction, and then returned the solution back to room temperature. After that, add pure water (about 1 L) and acidify the aqueous phase with hydrochloric acid to pH 1.0-2.0, after that, separate the two phases and the discard the organic phase. Basify the aqueous phase to pH 11.0-12.0 with saturated aqueous sodium hydroxide solution (3×100 mL). After that, extract the solution with ether (3×1 L), use centrifuging equipment to achieve the two-phase separation effect, dry the organic phase with anhydrous sodium sulfate, and then concentrate it under reduced pressure to obtain a crude product, which is separated and purified by liquid column chromatography (SiO$_2$, EtOAc/CH$_3$OH=95/5) and reacts to form a 2β-Carbomethoxy-3β-(4-fluoropenyl) tropane (or β-CFT in brief), 1.1 g, the yield is 36%.

The analysis data of the 2β-Carbomethoxy-3β-(4-fluoropenyl) tropane of this invention is as follows: IR (KBr): vCO=1732 cm-1.

$^1$H NMR (CDCl$_3$): 7.17 (dd, 2H, C6H4), 7.32 (dd, 2H, C$_6$H$_4$), 3.56 (m, 1H, C$_3$—H), 3.50 (s, 3 H, C$_{16}$—H$_3$), 3.35 (m, 1 H, C$_6$—H), 2.96 (m, 1 H, C$_8$—H), 2.87 (m, 1 H, C$_2$—H), 2.55 (m, 1 H, C$_7$-Ha), 2.22 (s, 3 H, C$_{15}$—H$_3$), 2.15 (m, 2 H, C$_4$—H$_a$ and C$_5$—H$_a$), 1.63 (m, 3 H, C$_4$—H$_b$, C$_5$—H$_b$ and C$_7$—H$_b$).

$^{13}$C NMR (CDCl$_3$): δ172.7 (CO), 163.3, 160.13, 139.2, 129.45 (C$_6$H$_4$) and 115.4 (CF), 65.91, 62.86, 53.51, 51.79 (OCH$_3$), 42.58 (NCH$_3$), 34.84, 33.87, 26.55, 25.79.

ESI-MS: m/z 277 (M$^+$).

Figure 3:
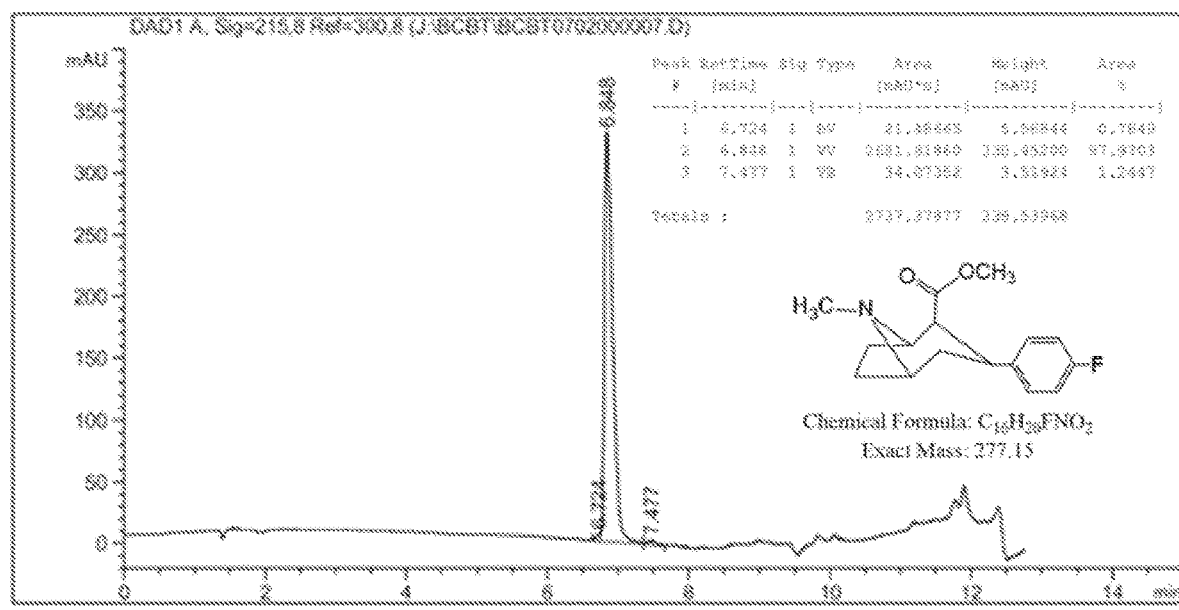
FIG. 3: The purity solution diagram of 2β-Carbomethoxy-3β-(4-fluoropenyl) tropane in this invention.

Moreover, refer to FIG. 3, which is the purity solution diagram of 2β-Carbomethoxy-3β-(4-fluoropenyl) tropane in this invention. As shown in the figure, the 2β-Carbomethoxy-3β-(4-fluoropenyl) tropane (briefly, β-CFT) prepared by this invention is analyzed for purity (HPLC). The analysis data is as follows: Mobile A: H$_2$O, formate NH$_4$, acetic acid, pH 5.0, Mobile B: Methanol; C18 column, 15 cm, 4.6 mm, 5 mm, 5 mL; Detection: UV 215 nm; flow rate: 1 ml/min, RT=6.848 min.

It can be seen from FIG. 3 and the above analysis data that the purity of the 2β-Carbomethoxy-3β-(4-fluoropenyl) tropane (briefly, β-CFT) in this case is as high as 97.97%. Moreover, while using the β-CFT system of this invention as a precursor of contrast media for positron Parkinson's disease, when β-CBT is marked with F-18, the non-radioactive standard used for comparison enables the development of PET and serves as an alternative to nuclear medicine for the diagnosis of Parkinson's disease.

Therefore, this invention is innovative, progressive and available for industrial use. It should undoubtedly meet the patent application requirements of ROC Patent Act. We hereby file the patent application in this invention in accordance with the law and anticipate the Authority's patent granting.

However, the above are only preferred embodiments of this invention, and are not used to limit the scope of implementation of this invention. For example, all shapes, structures, features and spirits described in the scope of the patent application of this invention are equal Changes and modifications shall be included in the scope of the patent application of this invention.

SYMBOLS

S1~S3 Step flows

What is claimed is:

1. A preparing method of non-radioactive standard β-CFT, the steps include:

Taking a cocaine hydrochloride and a hydrochloric acid for a hydrolysis reaction to form an ecgonine hydrochloride;

Taking the ecgonine hydrochloride and a phosphorus oxychloride for a dehydration reaction to form a (R)-(-)-Anhydroecgonine methyl ester; and And taking the (R)-(-)-Anhydroecgonine methyl ester and a Grignard reagent making a bonding reaction to form a 2β-Carbomethoxy-3β-(4-fluoropenyl) tropane.

2. The preparing method of non-radioactive standard β-CFT stated in claim 1, wherein after the step of taking the ecgonine hydrochloride and a phosphorus oxychloride for a dehydration reaction, it further comprises the step of: adding an anhydrous methanol for an esterification reaction.

3. The preparing method of non-radioactive standard β-CFT stated in claim 1, wherein in the step of taking the (R)-(-)-Anhydroecgonine methyl ester and a Grignard reagent for a bonding reaction, the Grignard reagent is a 4-fluorophenyl magnesium bromide.

4. The preparing method of non-radioactive standard β-CFT stated in claim 3, wherein before the step of taking the (R)-(-)-dehydrated ecgonine methyl ester and a Grignard reagent for a bonding reaction, the method further includes the step of: dissolving the Grignard reagent in anhydrous dichloromethane, and cooling it down to −50° C.

5. The preparing method of non-radioactive standard β-CFT stated in claim 3, wherein in the step of taking the (R)-(-)-dehydrated ecgonine methyl ester and a Grignard reagent for a bonding reaction, the bonding reaction is carried out under nitrogen environment.

6. The preparing method of non-radioactive standard β-CFT stated in claim 3, wherein in the step of taking the (R)-(-)-dehydrated ecgonine methyl ester and a Grignard reagent for a bonding reaction, a trifluoroacetic acid is further added for the bonding reaction.

* * * * *